United States Patent [19]
Takayama et al.

[11] Patent Number: 5,601,983
[45] Date of Patent: Feb. 11, 1997

[54] METHOD FOR SPECIMEN MEASUREMENT

[75] Inventors: Hidehito Takayama, Chigasaki; Matsuomi Nishimura, Ohmiya; Kazumi Tanaka, Yokohama; Toshikazu Ohnishi, Machida; Takeshi Miyazaki, Ebina, all of Japan

[73] Assignee: Canon Kabushiki Kaisha, Tokyo, Japan

[21] Appl. No.: 395,631

[22] Filed: Feb. 28, 1995

Related U.S. Application Data

[63] Continuation of Ser. No. 948,313, Sep. 22, 1992, abandoned.

[30] Foreign Application Priority Data

Oct. 1, 1991  [JP]  Japan .................... 3-253625

[51] Int. Cl.$^6$ .................... C12Q 1/68
[52] U.S. Cl. .................... 435/6; 435/7.1; 435/961; 435/968; 436/518; 436/524; 436/528; 436/533; 436/536; 436/542; 436/172; 436/800; 436/804; 436/805; 436/823; 356/337; 356/441
[58] Field of Search .................... 435/6, 7.1, 7.9, 435/961, 967, 968; 436/518, 526, 528, 533, 536, 542, 172, 800, 801, 804, 823, 524; 356/337, 441

[56] References Cited

U.S. PATENT DOCUMENTS

| | | | |
|---|---|---|---|
| 4,385,126 | 5/1983 | Chen et al. | 436/518 |
| 4,628,037 | 12/1986 | Chagnon et al. | 436/526 |
| 5,123,731 | 6/1992 | Yoshinaga et al. | 356/73 |
| 5,223,398 | 6/1993 | Kortright et al. | 435/7.24 |

FOREIGN PATENT DOCUMENTS

| | | |
|---|---|---|
| 0226903 | 1/1987 | European Pat. Off. . |
| 0271974 | 6/1988 | European Pat. Off. . |
| 2627286 | 8/1989 | France . |
| 2019562 | 10/1979 | United Kingdom . |
| WO9112530 | 8/1991 | WIPO . |

OTHER PUBLICATIONS

Seradyn, Inc. "Microparticle Immunoassay Techniques" 2nd Ed. 1988.

*Primary Examiner*—James C. Housel
*Assistant Examiner*—Rachel Heather Freed
*Attorney, Agent, or Firm*—Fitzpatrick, Cella, Harper & Scinto

[57] ABSTRACT

In a method for measuring a specified component in a specimen by reacting the specimen with a first reagent formed by binding a substance active to the specified component, with carrier particles and a second reagent formed by labelling a substance active to the specified component with a first label, and measuring the substances in the complexes obtained in the reaction, there is disclosed a method featured by labelling the carrier particles with a second label different from the first label, and detecting the second label and then the first label utilizing the detection of the second label as a trigger.

This method enables a highly precise measurement without the influence of noise components in the detection of specified trace components in the specimen, utilizing an antigen-antibody reaction or a nucleic acid hybridization.

3 Claims, 12 Drawing Sheets

IST REACTION (ANTIGEN-ANTIBODY REACTION WITH SPECIMEN)

2ND REACTION (REACTION WITH LABELLED ANTIBODY)

FLUORESCENT MEASUREMENT

METHOD FOR SPECIMEN MEASUREMENT

This application is a continuation of application Ser. No. 07/948,313 filed Sep. 22, 1992, now abandoned.

BACKGROUND OF THE INVENTION

1. Field of the Invention

The present invention relates to a technical field of specimen measurement for determining a specified trace component in the specimen utilizing, for example, an antigen-antibody reaction or hybridization of nucleic acid.

2. Related Background Art

The recent advances in the detection technologies of specified trace components in the specimen are playing a significant role in the field of clinical tests, for early diagnosis or discovery of various deseases. Since it was published in 1958 by S. A. Berson et al. that insulin was determined with radioactive iodine labelling, there have been established determinations of plasma protein such as IgE, IgG, CRP and microglobulin, tumor markers such as AFP, CEA and CA19-9, hormones such as TSH and $T_3$, pharmaceutical substances in blood, virus as such as HBV and HIV, antibodies therefor, and nucleic acids such as DNA and RNA, with possibility for automated processing of plural specimens.

Most of these trace components are determined by immunoassays utilizing antigen-antibody reactions, or by methods utilizing nucleic acid-nucleic acid hybridization. In such analytical methods, for example, an antigen, an antibody or a single-chain nucleic acid capable of specifically binding with the object substance to be determined, is used as a probe, and is fixed on a solid surface such as small particles, beads or a reactor wall., and an antigen-antibody reaction or a nucleic acid hybridization with said object substance is effected. In such reaction there is employed a labelled antigen, a labelled antibody or a labelled nucleic acid, bearing a labelling substance of a high detection sensitivity such as an enzyme, a fluorescent substance or a light-emitting substance to detect an antigen-antibody complex or a double-chained nucleic acid, thereby determining the amount of the object substance to be determined.

FIG. 9 illustrates a typical example of fluoroimmunoassay (sandwich immunoassay) in which the object substance is an antigen. A first reagent is prepared, in which an antibody 24 constituting a first substance capable of specifically binding with an antigen 22 contained in the specimen, is fixed on carrier particle 21 in advance, and is mixed with a specimen such as serum to induce an antigen-antibody reaction with the antigen 22 therein (1st reaction). Then, a second reagent in which an antibody 23 capable of specifically binding with the antigen 22 is labelled with a fluorescent substance 25, is mixed to form a complex (2nd reaction). After 2nd reaction, an amount of the antigen 22 in the specimen is determined by the fluorescent measurement of the complex.

FIG. 10 shows an example of the fluorescent measurement of the above-mentioned sandwich immunoassay, utilizing so-called flow cytometry technology. A sample liquid containing complexes 31, 32 obtained through the reactions explained above is contained in a reaction liquid bath 38. It is to be noted that said sample liquid also contains various substances in the specimen, carrier particles, labelling substance or the like. The reaction liquid bath 38 is pressurized by a pump 39 to feed the sample liquid into a flow cell 35. In said flow cell, there flows sheath liquid 34 to generate a laminar flow due to sheath flow principle, whereby a plurality of complexes 31, 32 flow in a line. Said flow is irradiated by a laser light source 36 with a laser beam of a wavelength capable of exciting the labelling fluorescent substance. When the complex 31 is irradiated by the laser beam, a scattered light 37a is generated by the carrier particle, and a fluorescent light 37b is simultaneously emitted from the labelling substance 33a. However, when the labelling substance 33a, object substance 33b or carrier particle 33c each unreacted flows alone, the scattered light 37a and the fluorescent light 37b are not generated at the same time, or only at a very low intensity. Consequently, the complexes 31, 32 alone can be selectively measured, independently from other noise components, by collect the data only when the scattered light and the fluorescent light are generated at the same time and exceed a certain level.

FIG. 11 is a wave form chart indicating the signals of the scattered and fluorescent lights in the measurement shown in FIG. 10. In an ideal case shown in FIG. 11, the intensity of the forward scattered light is high when a complex reaches the irradiated area of the flow cell and is low except at said area, since a strong scattered light 51 is generated by the carrier particle. Therefore, a trigger signal 52 is generated when the intensity of the forward scattered light is beyond a predetermined level, and the intensity of the fluorescent light 53 is measured at the timing of said trigger signal 52, whereby the intensity of the fluorescent light from the complex can be selectively determined. If fluorescent light is generated, it can be judged the object substance is present and an antigen-antibody reaction or a nucleic acid hybridization reaction has been induced. On contrary, no fluorescent light is generated, it can be judged that such reaction has not been induced. The object substance can be determined by statistical processing of a multitude of measurements.

In practice, however, the ideal output as shown in FIG. 11 is not obtainable, since the increase in the light intensity is caused, as shown in FIG. 12, by factors other than the forward scattered light generated by the complexes themselves. As example of such factors there are floating substances present in the original reaction liquid and bubbles generated therein. In such a case, as shown in FIG. 12, the forward scattered light shows not only a peak 61 resulting from the complexes but also a peak 62 resulting from the floating substances or the bubbles. Consequently, in addition to a trigger signal 63 corresponding to the complexes, there is generated a false trigger signal 64 based on such floating substances or bubbles, so that the fluorescent intensity (zero-level) at that time is read. This causes a mistake as if there were carrier particles having not induced the antigen-antibody reaction or the nucleic acid hybridization reaction, significantly affecting adversely the precision of quantitative measurement.

SUMMARY OF THE INVENTION

A first object of the present invention is to resolve the above-mentioned drawbacks of the prior art.

A second object of the present invention is to provide a method and an apparatus capable of specimen measurement with a high accuracy.

A third object of the present invention is to provide a reagent for said specimen measurement.

Still other objects of the present invention will become fully apparent from the following description of the embodiments.

DETAILED DESCRIPTION OF THE PREFERRED EMBODIMENTS

Figure 1:
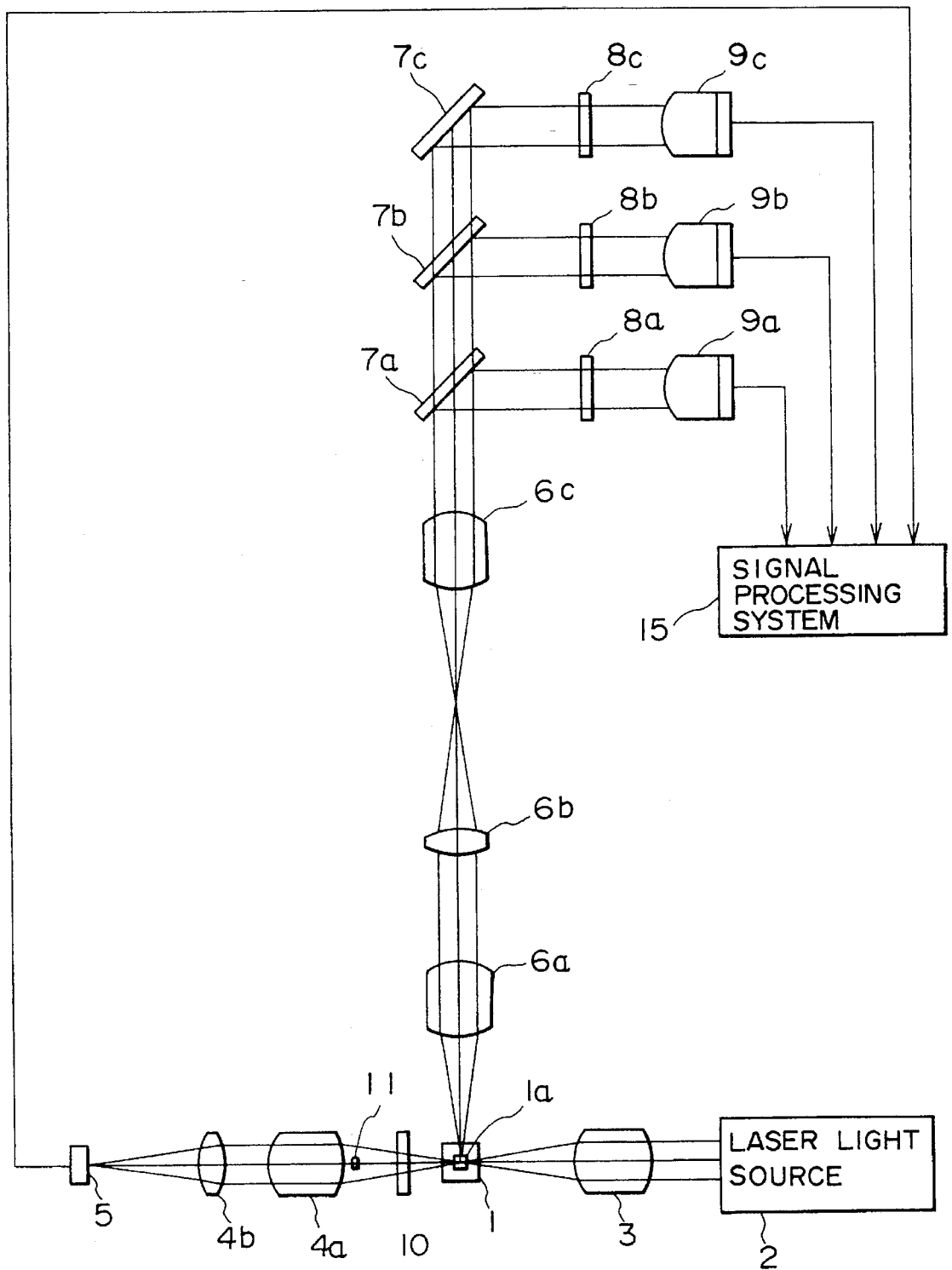
FIG. 1 is a schematic view of a measuring apparatus constituting a first embodiment of the present invention.

Embodiments of the present invention will be explained with reference to the attached drawings.

First Embodiment

A first embodiment employs a substance converting wavelength of irradiating light, more specifically a fluorescent substance, as a labelling substance for carrier particles, and the carrier particles are identified by a fluorescent light generated.

The present embodiment employs following reagents. A first reagent is obtained by binding a first substance which binds to an object substance to be detected in a specimen, with polystyrene particles of a particle size, for example, of 1 µm, labelled with a fluorescent substance. The fluorescent-labelled carrier particles can be obtained by physically or chemically binding polymer particles, for example, of polystyrene with the fluorescent substance, or by copolymerizing a fluorescent monomer upon polymerization of the polymer particles. Said fluorescent substance can be suitably selected, for example, from cyanine dyes, acridine dyes and rhodamine dyes, so as to have a fluorescent characteristic different from that of a second fluorescent substance to be explained later. The binding of the first substance which binds to the object substance, with the fluorescent particles is done in the already known physical or chemical method.

Examples of said first substance which binds to the object substance, include natural or synthesized peptides, proteins, enzymes, sugars, lecithine, viruses, bacteria, nucleic acid, DNA, RNA and antibodies. Among these substances, clinically particularly useful ones are listed below: immunoglobulins such as IgG or IgE; plasma proteins and their antibodies such as compliment, CRP, pheritin, $\alpha_1$ or $\beta_1$ microglobulin; principal markers and their antibodies such as α-phetoprotein, carcinoembryonic antigen (CEA), CA19-9 or CA-125; hormones and their antibodies such as luteinizing hormone (LH), follicle-stimulating hormone (FSH), human chorionic gonadotropin (HCG), estrogen or insulin; virus-infection related substances and their recombinant antigens and antibodies such as HBV-related antigens, HIV or ATL; bacteria and their antibodies such as diphtheria bacillus, botulinus bacillus, mycoplasma or *Treponema pallidum;* protozoa and their antibodies such as Toxoplasma, trichomonas, Leishmania, Trypanosoma or Malaria; anti-epileptics such as phenytoin or phenobarbital; anti-arrhythmic drugs such as quinidine; cardiovascular agents such as digoxin; vasodilators such as theophylline; antibiotics such as chloramphenicol or gentamycin, and antibodies of these drugs; enzymes, exotorins and their antibodies such as streptolysin O. A substance capable of causing an antigen-antibody reaction with the object substance in the specimen is suitably selected according to a kind of the object substance.

Also, in the case that the nucleic acid hybridization is utilized instead of the above-mentioned antigen-antibody reaction, there is employed a nucleic acid probe as the first substance having a base sequence complementary to that of the nucleic acid to be detected.

On the other hand, a second reagent is obtained by binding a labelling substance with a second substance which binds to the object substance to be detected and is different from the first substance. The labelling substance is, for example, a fluorescent substance of a fluorescent characteristic different from that of the fluorescent substance used for labelling the carrier particles, or a light-emitting substance. The binding is conducted chemically by a crosslinking agent such as polyamine or carbodiimide.

Both the first and second reagents are dispersed in a dispersion medium composed principally of water. To the dispersion medium may suitably added is a pH buffer, a protein, a surfactant or a water-soluble polymer compound. The reaction between the first reagent and the second reagent and the object substance proceeds depending on reactivity between the object substance and the substance active thereto contained in the reagent, and also depending on the concentration of the object substance. After reactions under respectively appropriate conditions, the reaction liquid is diluted with diluting liquid principally composed of water to obtain sample liquid.

FIG. 1 is a schematic view of the measuring apparatus of the present embodiment. In a flow area 1a of a flow cell 1, the sample liquid flows in a direction perpendicular to a surface of the drawing, in a state surrounded by sheath liquid with a high-speed laminar flow due to so-called sheath flow principle, whereby the various small substances contained in the sample liquid flow in a line in turn. A laser light source 2 is arranged in a direction perpendicular to the flow, and a laser beam emitted therefrom is converted by a lens 3 into a small oval spot to irradiate the flow area. The wavelength of the laser beam is so selected as to be capable of exciting both the fluorescent substance used for labelling the carrier particles and that used for labelling the second substance. In order to measure with dark field principle the forward scattered light generated by the small article passing through the irradiated position, there are arranged a wavelength selecting filter 10, a light stopper 11, condenser lenses 4a, 4b and a photodetector 5 in succession on the optical axis opposite to the lens 3 relative to the flow cell 1. The wavelength selecting filter 10 is constructed so that filters having different wavelength characteristics may be switched according to the purpose of the measurement. In the present embodiment, the wavelength selecting filter 10 is capable of selectively transmitting the wavelength λ of the laser beam.

On an optical axis perpendicular to the direction of flow of the sample liquid and to the irradiating direction of the laser beam, there are arranged, in the order from the flow cell 1, condenser lenses 6a, 6b, a collimating lens 6c, dichroic mirrors 7a, 7b with wavelength selecting characteristics and a mirror 7c. In the reflected directions of the dichroic mirrors 7a, 7b, there are provided barrier filters 8a, 8b and photodetectors 9a, 9b, and, in the reflected direction of the mirror 7c there are provided a barrier filter 8c and a photodetector 9c.

A scattered light is generated by the carrier particles, bubbles and dusts of the sample liquid, flowing in succession in the flow area 1a of the flow cell 1. Also, a fluorescent light 1 of a first wavelength is generated by the fluorescent dye used for labelling the carrier particles, and a fluorescent light 2 of a second wavelength is generated by the fluorescent labelling substance of the second substance. The fluorescent light 1 is subjected to wavelength selection by the dichroic mirror 7a and the barrier filter 8a, and to intensity detection by the photodetector 9a. Also, the fluorescent light 2 is subjected to wavelength selection by the dichroic mirror 7b and the barrier filter 8b, and to intensity detection by the photodetector 9b. The photodetector 9c, provided for detecting the intensity of the lateral scattered light, may be omitted since it is not used in the present embodiment.

The outputs of the photodetectors 9a, 9b, 9c are supplied to a signal processing system 15, which effects signal processing for specimen measurement as will be described later, based on the signals from the detectors.

Figure 2:
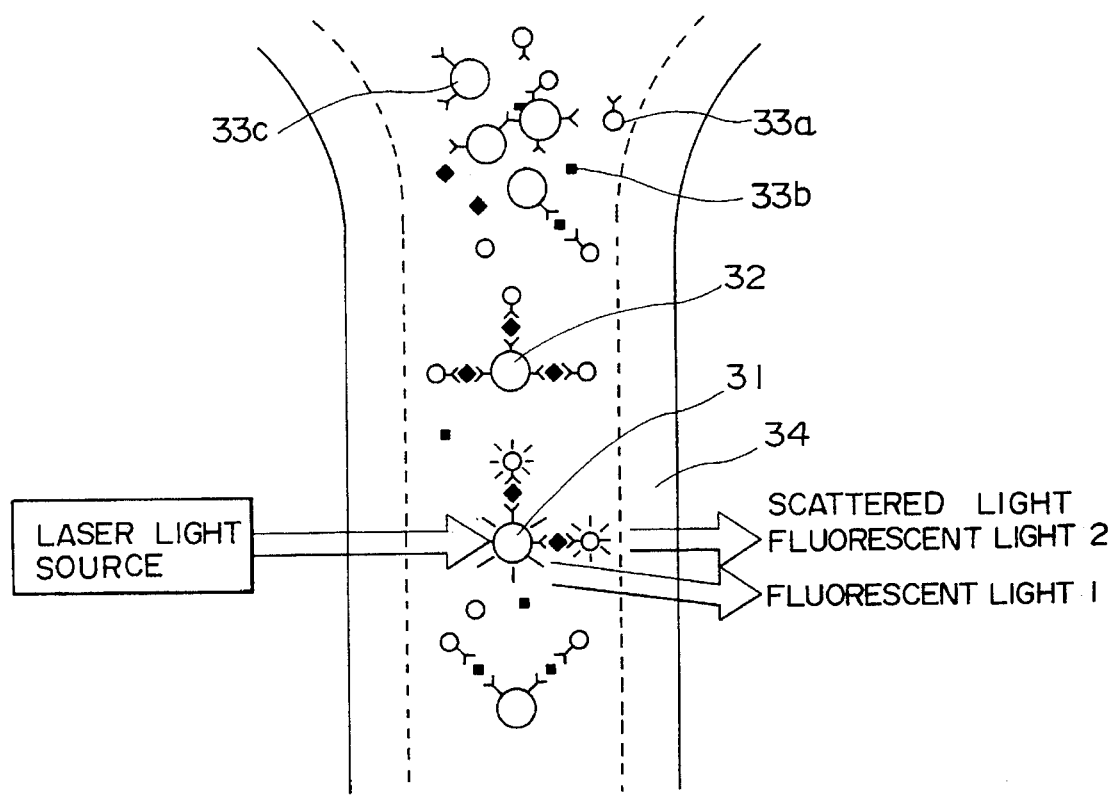
FIG. 2 is a view showing the principle of the measurement of the first embodiment.

FIG. 2 is a schematic view showing the principle of measurement of the present embodiment, illustrating the state in the flowing area of the flow cell. The sample liquid flowing in a surrounded state in the sheath liquid, contains the complexes 31, 32, the fluorescent labelled second substance 33a, the object substance 33b, the carrier particles 33c, and other substances such as bubbles and dusts, which flow in successive manner in the flowing area. In response to the irradiating laser beam, the carrier particle generates the scattered light and the fluorescent light 1, and the fluorescent substance generates the fluorescent light 2. Since the fluorescent substance and the object substance are very small, they generate no scattered light, or only very weakly. The complex 31 or 32, composed of the carrier particle, the object substance to be detected and the fluorescent substance, upon passing the irradiated portion, generates the scattered light, fluorescent light 1 and fluorescent light 2. When the fluorescent light 1 is detected, it is judged carrier particle and this is used as the trigger for detecting the fluorescent light 2 in the present embodiment. The carrier particle may also be identified by the logic product of the fluorescent light 1 and the scattered light.

Figure 3:
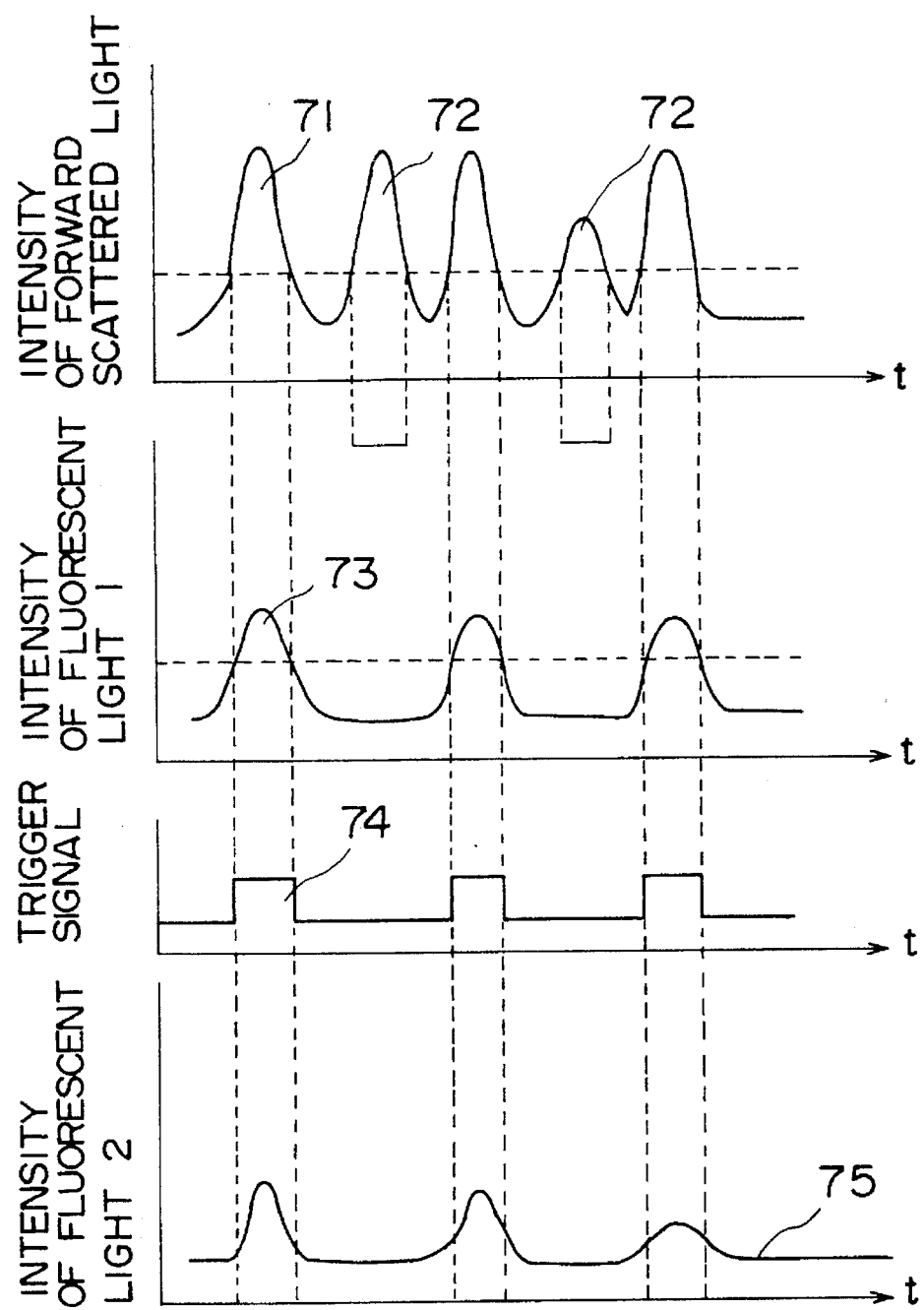
FIG. 3 is a wave form chart showing detection signals obtained by the measurement of the first embodiment.

FIG. 3 is a wave form chart showing the signals measured in the apparatus shown in FIG. 1. Conventionally, the intensity of the forward scattered light has been utilized for generating the trigger signal to detect the fluorescent light, but the accuracy of measurement has been insufficient because the trigger signal is also generated by the forward scattered light resulting from bubbles and dusts as shown by reference numeral 72 in FIG. 3. In the present embodiment, a trigger signal 74 is generated when the fluorescent light 1 exceeds a certain threshold value. The trigger signal may also be generated by the logic product of the (forward or lateral) scattered light and the fluorescent light 1. The intensity 75 of the fluorescent light 2 is measured at the timing of said trigger signal. Consequently, the present embodiment is capable of precisely determining the amount of labelling substance in the complex, thereby enabling highly accurate quantitative determination of the object substance in the specimen, without influence of noise components such as dusts and bubbles in the conventional case.

The following experiment was conducted to verify the effect of the above-explained embodiment. An aqueous dispersion of epoxylated polystyrene particles bound with a fluorescent substance FITC, having a particle size of 1.0 μm and a particle concentration of 0.5 wt. %, was diluted 10,000 times and measured by said apparatus. For comparing the conventional method and the method of the present embodiment, the number of trigger signals generated by the intensity of the forward scattered light was at first counted for 30 seconds, and the number of trigger signals generated by the intensity of the fluorescent light 1 was then counted similarly for 30 seconds. As a result, the obtained count was larger, by about 20%, in the conventional method based on the forward scattered light. The larger count is considered to be ascribable to the influence of the noise components such as dusts and bubbles, contained in the aqueous dispersion and giving rise to additional counts. As explained above, the use of labelled particles prepared by binding the fluorescent substance FITC with the carrier particles, enabled highly precise determination with a high S/N ratio.

Second Embodiment

A second embodiment of the present invention, explained in the following, utilizes a wavelength converting substance for irradiating light, more specifically, a substance generating a harmonic, such as SHG or THG, for labelling carrier particles, and the carrier particles are identified by detecting the wavelength-converted light.

In the present embodiment, the first reagent is obtained, for example, by binding a first substance active to an object substance in a specimen with small particles of a particle size of about 1 μm, having SHG activity (for generating a second-order harmonic). An example of such particles with SHG activity is polymer particles containing a polar substance of a large second-order hyperpolarizability $\beta$. More specifically, such substance with SHG activity can be prepared by doping polyoxyethylene or lactone polymer with p-nitroaniline, or by emulsion polymerization of chemically modified p-nitroaniline with styrene monomer. The binding of the first substance active to the object substance with the particles with SHG activity can be achieved by a known physical or chemical method.

Figure 4:
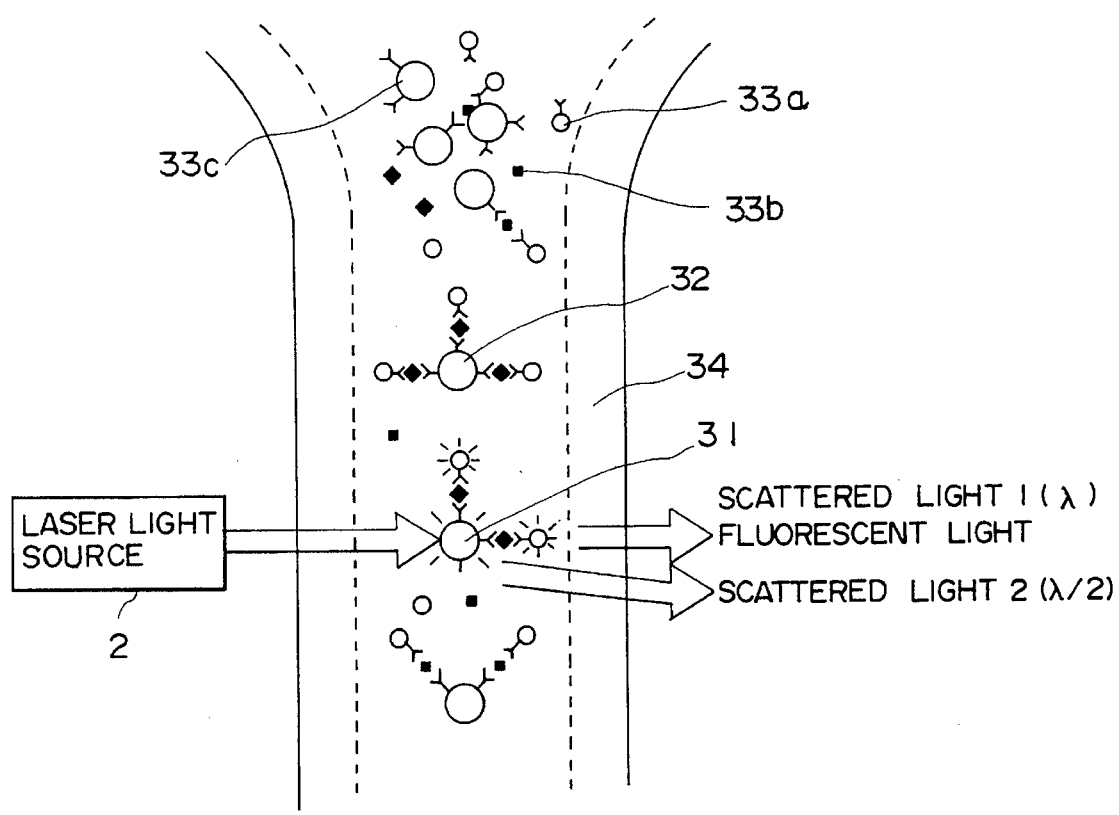
FIG. 4 is a view showing the principle of the measurement of a second embodiment.

FIG. 4 is a schematic view showing the principle of measurement of the present embodiment, and illustrating the state in the flowing portion of the flow cell. The configuration of the entire apparatus is similar to that shown in FIG. 1, except that the wavelength selecting filter 10 is adapted to selectively transmit the light of a half wavelength $\lambda/2$ of the original wavelength $\lambda$ of the laser beam, and the photodetector 5 is adapted to detect the wavelength-converted light generated by the SHG substance. In the case that the THG substance generating a third-order hypertonic wave is employed for labelling the carrier particles, there is employed a wavelength selecting filter 10 capable of selecting a wavelength $\lambda/3$. The sample liquid flowing in a state surrounded by the sheath liquid, contains the complexes 31, 32, the fluorescent-labelled second substance 33a, the object substance 33b, the carrier particles 33c and other substances such as bubbles and dusts, which flow in successive manner in the flowing portion. In response to the irradiating laser beam of a wavelength $\lambda$, the carrier particle generates a scattered light 1 of a wavelength $\lambda$ and a scattered light 2 of a SHG-converted wavelength $\lambda/2$, and the fluorescent substance generates a fluorescent light. Since the fluorescent substance and the object substance are very small, they generate no scattered light, or only very weakly. The complex 31 or 32, composed of the carrier particle, the object substance and the fluorescent substance, upon passing the irradiated portion, generates all the scattered lights 1, 2 and the fluorescent light. The scattered light 2 ($\lambda/2$) is selected by the wavelength selecting filter 10 shown in FIG. 1. It is judged carrier particle when the scattered light 2 is detected by the photodetector 5. This is used as a trigger for detecting the fluorescent light in the present embodiment. It is also possible to provide an optical system capable of simultaneously detecting the scattered lights 1 and 2, and to use the logic product of the intensities of the scattered lights 1 and 2 as said trigger.

Figure 5:
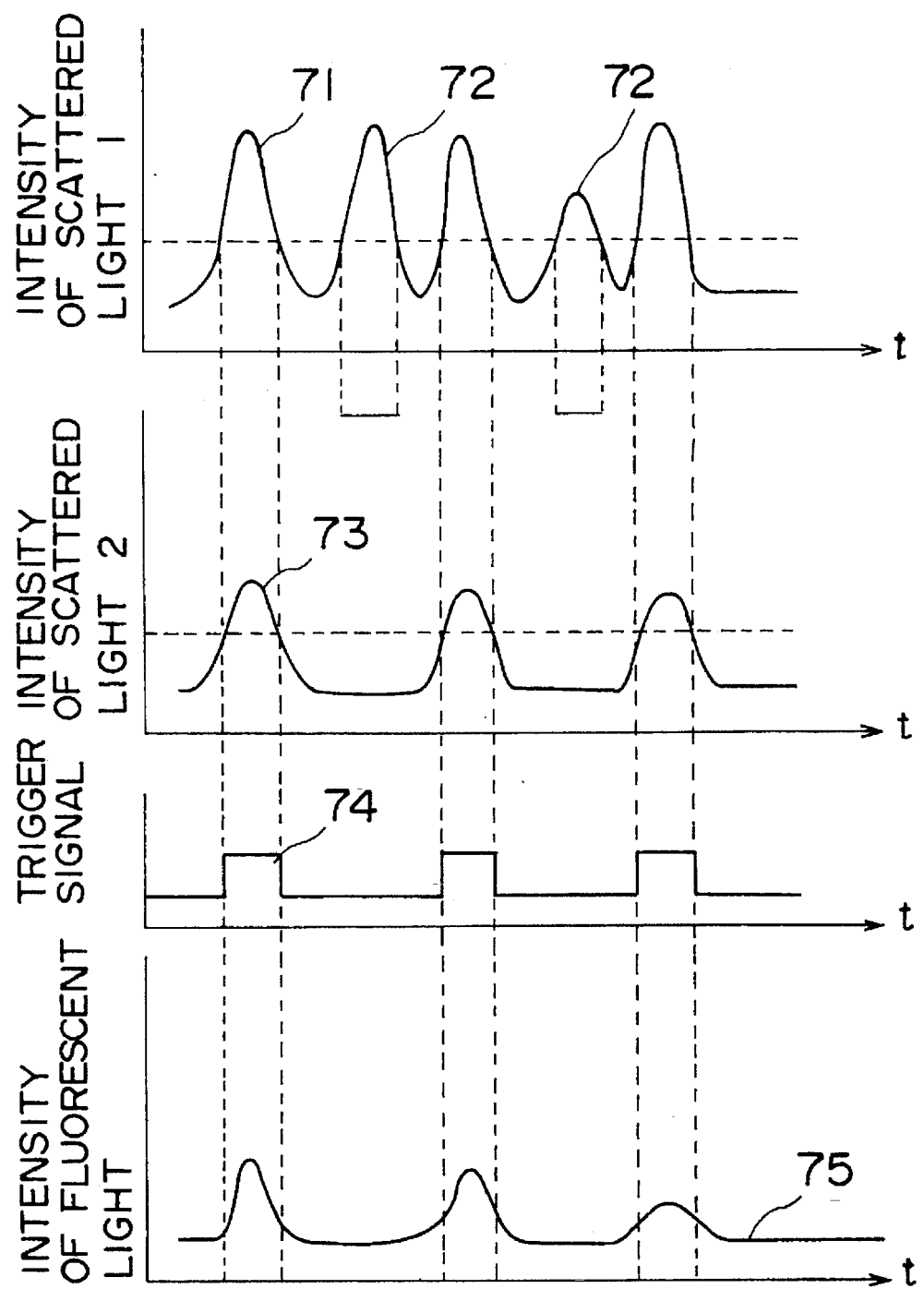
FIG. 5 is a wave form chart showing detection signals obtained by the measurement of the second embodiment.

FIG. 5 is a wave form chart showing the signals measured in the apparatus shown in FIG. 1. Conventionally, the intensity of the forward scattered light (λ) has been utilized for generating the trigger signal to detect the fluorescent light, but the accuracy of measurement has been insufficient because the trigger signal is also generated by the forward scattered light resulting from bubbles and dusts as shown by reference numeral 72 in FIG. 5. In the present embodiment, a trigger signal 74 is generated when the scattered light 2 of the converted wavelength λ/2 exceeds a certain threshold value, and the intensity 75 of the fluorescent light is measured at the timing of said trigger signal. Consequently, the present embodiment is capable of precisely determining the amount of the labelling substance in the complex, thereby enabling highly accurate quantitative determination of the object substance in the specimen, without the influence of noise components such as bubbles and dusts in the conventional case.

Following experiment was conducted for verifying the effect of the above-explained embodiment. Aqueous dispersion of polystyrene particles, having a particle size of 1.0 μm and a particle concentration of 0.5 wt. %, given SHG activity by p-nitroaniline doping, was diluted 10,000 times and measured by said apparatus. For comparing, the conventional method and the method of the present embodiment, at first there was employed a wavelength selecting filter 10 capable of selecting the wavelength λ, and the number of the trigger signals generated by the intensity of the forward scattered light 1 of the wavelength λ, was counted for 30 seconds. Then a wavelength selecting filter 10 capable of selecting a wavelength λ/2 was employed, and the number of the trigger signals generated by the intensity of the forward scattered light 2 of the wavelength λ/2, was similarly counted for 30 seconds. As a result, the count in the conventional method, utilizing the trigger signals based on the forward scattered light 1 was larger by about 20%. The larger count is considered to be ascribable to the influence of the noise components, such as dusts and bubbles contained in the aqueous dispersion and giving rise to additional counts. As explained above, the use of labelled particles, prepared by coupling a SHG active substance to the carrier particles, enabled highly precise determination with a high S/N ratio.

Third Embodiment

A third embodiment of the present invention, explained in the following, utilizes a magnetic substance for labelling carrier particles, and the carrier particles are identified by magnetic detection.

In the present embodiment, a first reagent is obtained by binding a first substance which binds to an object substance to be detected in a specimen with small particles of a particles, for example, of about 1 μm, containing a magnetizable substance. The magnetic substance can be various compounds such as magnetite or γ-ferrite, or metals such as iron or cobalt, and a substance stable to the specimen can be suitably selected. Also, the binding of the first substance which binds to the object substance with the magnetic particles can be achieved by a known physical or chemical method.

Figure 6:
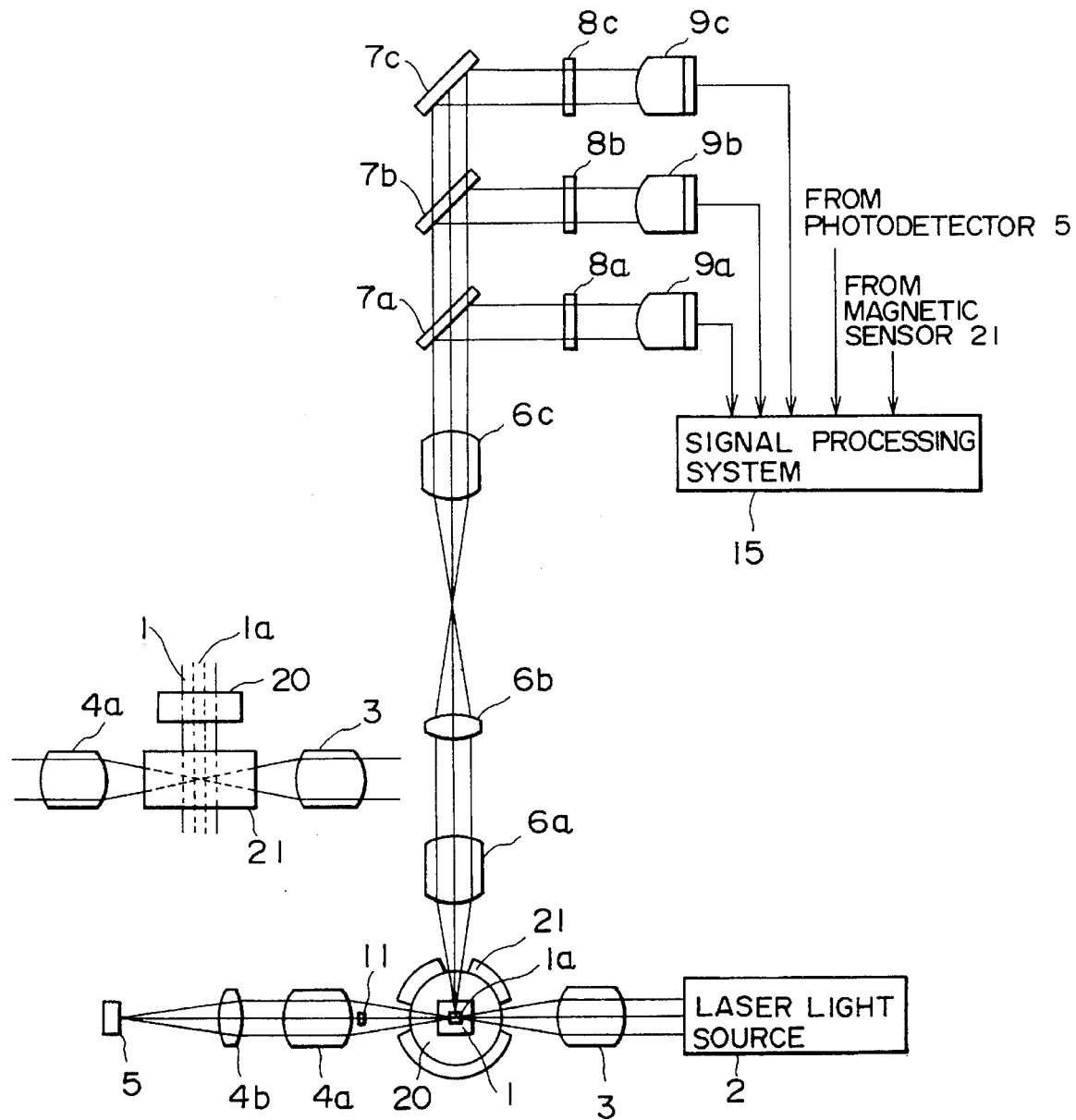
FIG. 6 is a schematic view of a measuring apparatus constituting a third embodiment.

FIG. 6 shows the configuration of the measuring apparatus of the present embodiment, wherein same components as those in FIG. 1 are represented by same numbers. The solid particles in the complexes in the reaction liquid flowing in the flow cell 1 are magnetized by a magnet 20, and the complexes are detected by a magnetic sensor 21 comprising a magnetic flux meter. The magnet 20 may be omitted if pre-magnetized carrier particles are employed. Outputs of the photodetectors 5, 9a, 9b, 9c and the magnetic sensor 21 are supplied to the signal processing system 15, which effects signal processing for the specimen measurement, as will be described later, based on the signals of said detectors.

Figure 7:
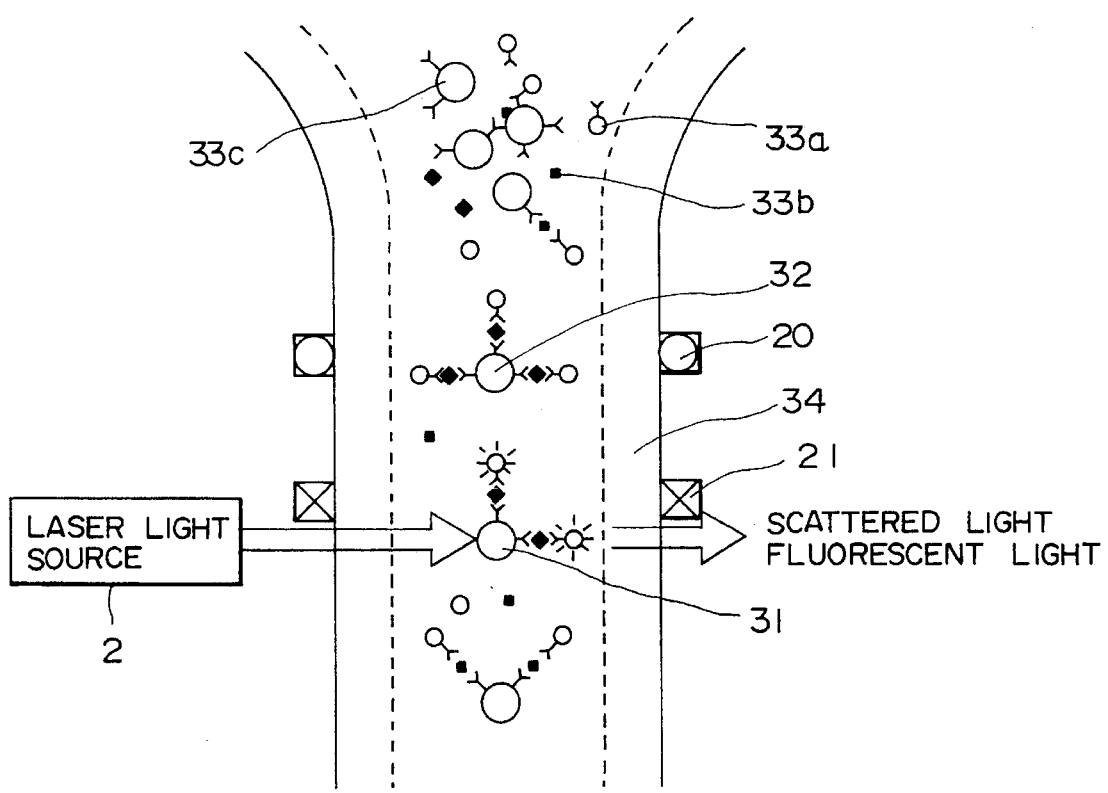
FIG. 7 is a view showing the principle of the measurement of the third embodiment.

FIG. 7 schematically shows the principle of measurement of the present embodiment employing the carrier particles containing the above-mentioned magnetizable substance (magnetic particles), illustrating the state in the flowing portion of the flow cell. The sample liquid flowing in a state surrounded by the sheath liquid, contains the complexes 31, 32, the fluorescent-labelled second substance 33a, the object substance 33b, the carrier particles 33c and other substances such as bubbles and dusts, which flow in successive manner in the flowing portion. In response to the irradiating laser beam, the carrier particle generates the scattered light as in the conventional method, and the fluorescent substance generates the fluorescent light. Since the fluorescent substance and the object substance are very small, they generate no scattered light, or only very weakly. The complex 31 or 32 composed of the carrier particle, the object substance and the fluorescent substance, upon passing the irradiated position, generates both the scattered light and the fluorescent light. In the present embodiment, the solid particles contain magnetizable substance, and the magnetic intensity of the solid particles is measured by means of the magnet 20 and the magnetic sensor 21, whereby a peak 73 in the magnetic intensity indicates the presence of the solid particles. This is used as a trigger for fluorescent light detection. The carrier particle may also be identified by the logic product of the scattered light and the magnetic intensity.

Figure 8:
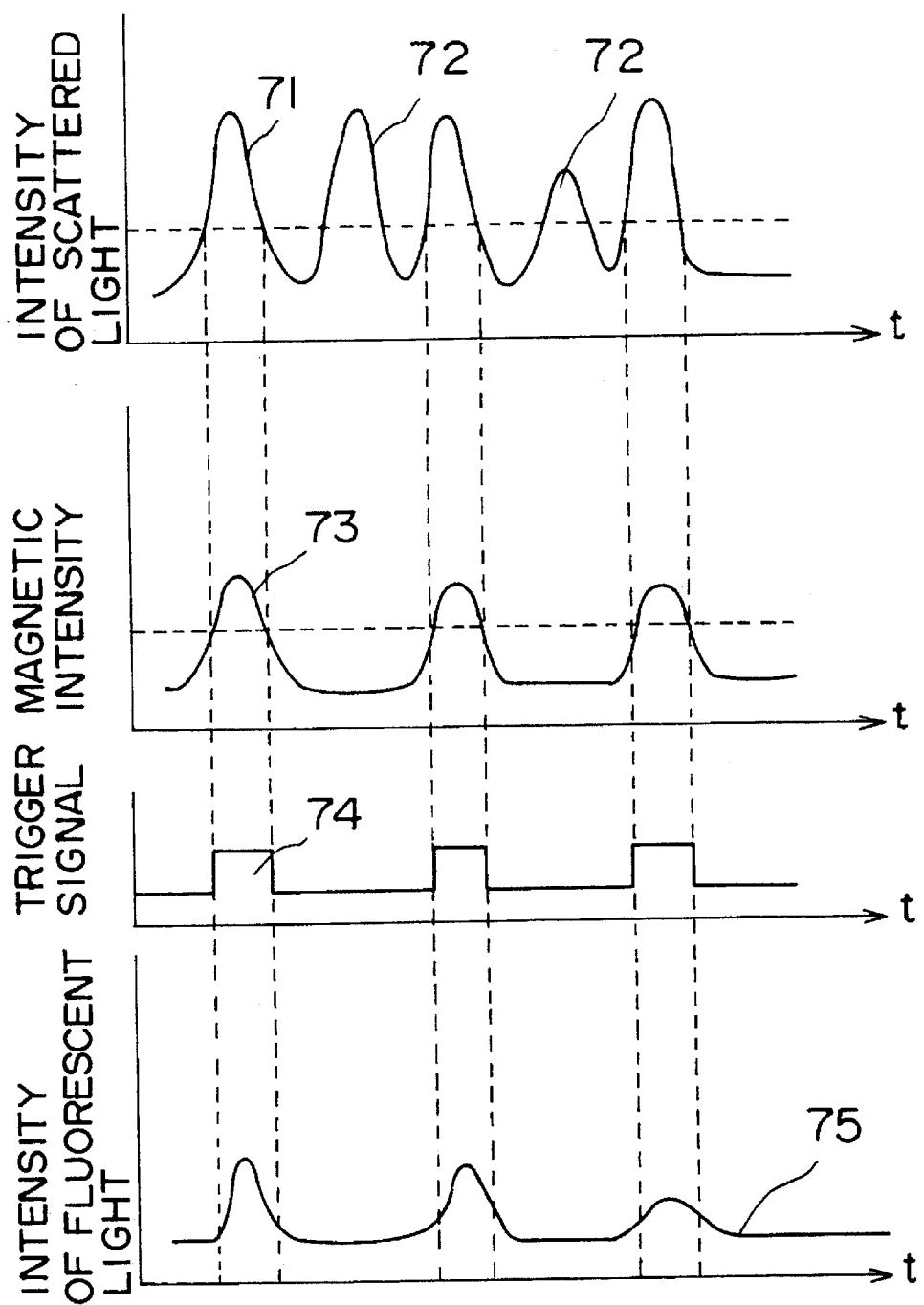
FIG. 8 is a wave form chart showing detection signals obtained by the measurement of the third embodiment.
Figure 9:
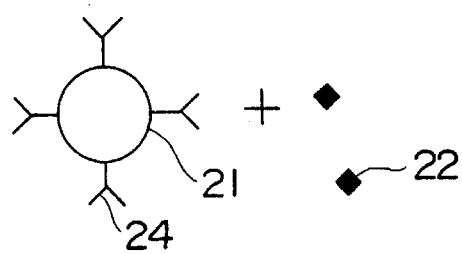
FIG. 9 is a view showing the principle of the conventional sandwich immunoassay.
Figure 9:
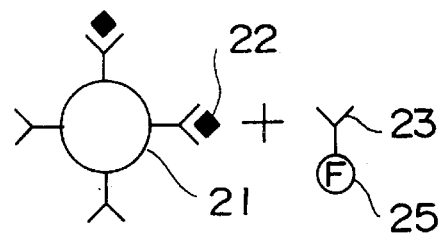
Figure 9:
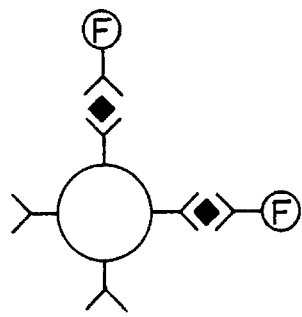
Figure 10:
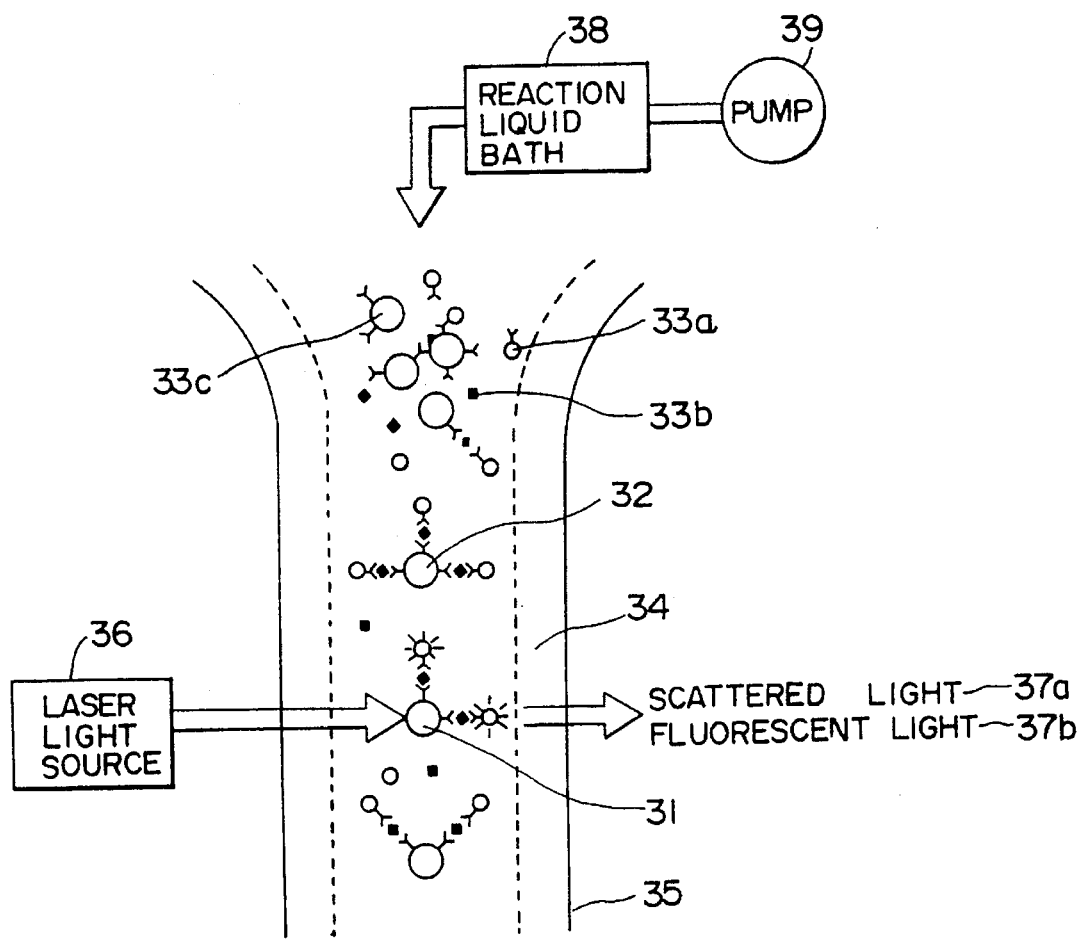
FIG. 10 is a view showing the principle of the conventional fluorescent measurement utilizing the flow cytometry technology.
Figure 11:
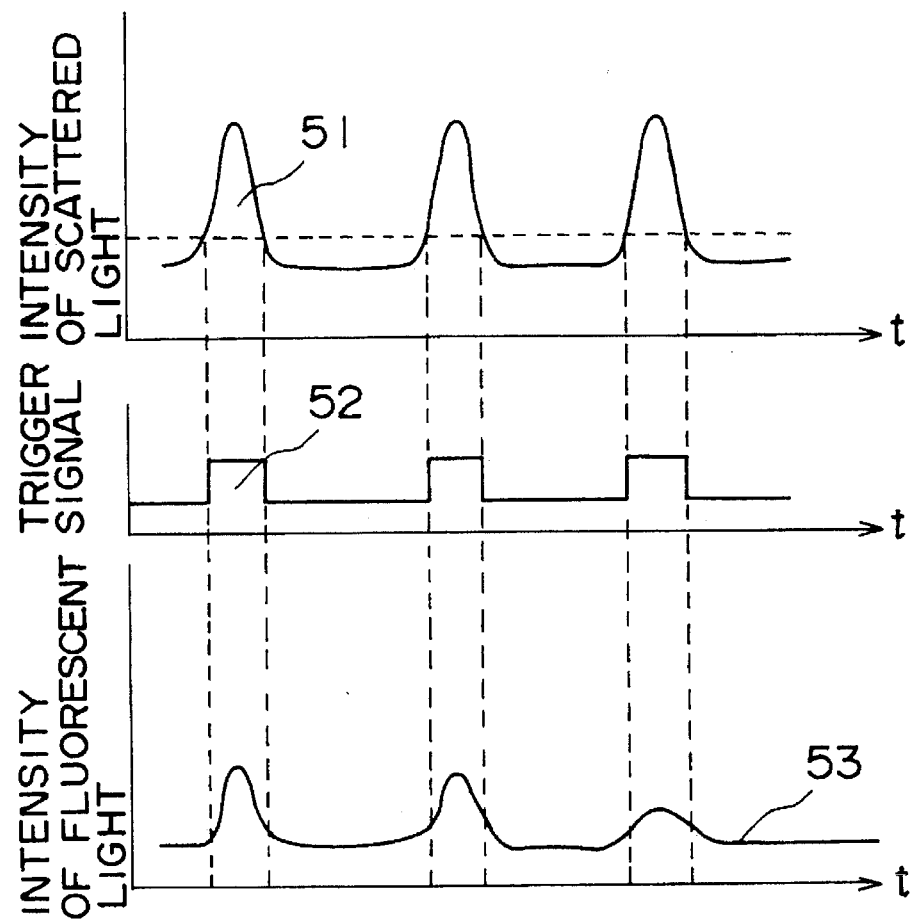
FIG. 11 is a wave form chart showing an ideal measurement in the prior art.
Figure 12:
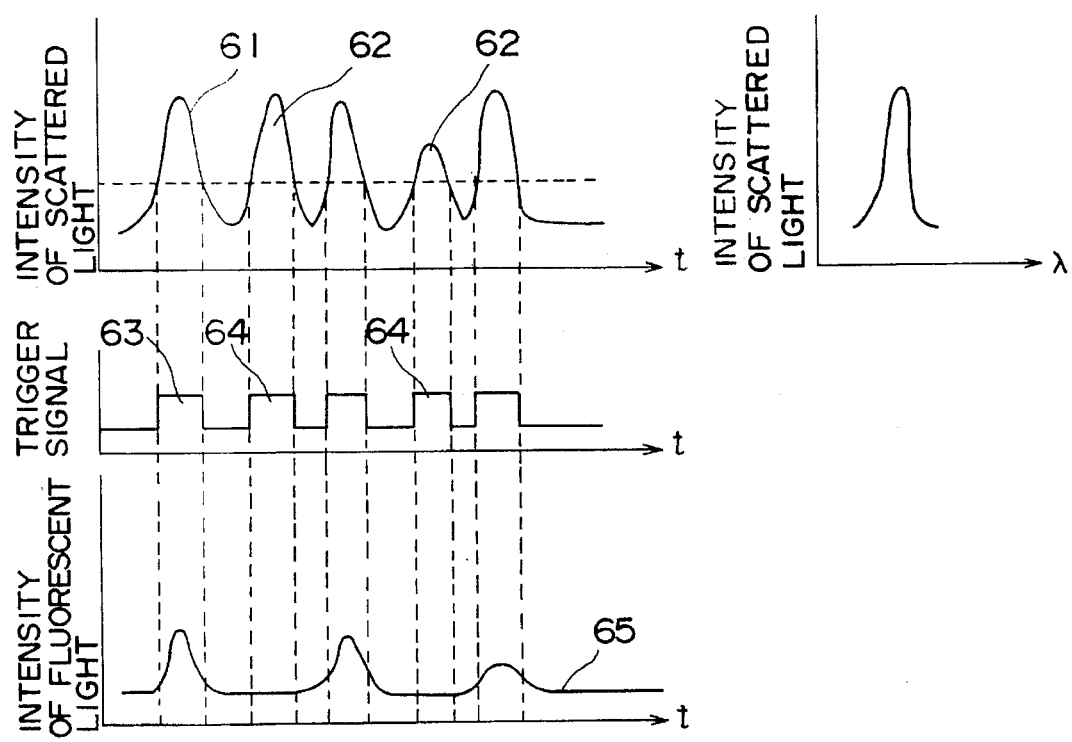
FIG. 12 is a wave form chart showing an actual measurement in the prior art.

FIG. 8 is a wave form chart of the signals measured in the apparatus shown in FIG. 6. Conventionally, the intensity of the forward scattered light has been utilized for generating the trigger signal to detect the fluorescent light, but the accuracy of measurement has been insufficient because the trigger signal is also generated by the forward scattered light resulting from bubbles and dusts, as shown by reference numeral 72 in FIG. 8. In the present embodiment, a trigger signal 74 is generated when the magnetic intensity of the passing carrier particle exceeds a certain threshold value. The trigger signal may also be generated by the logic product of the magnetic intensity and the scattered light. The intensity 75 of the fluorescent light is measured at the timing of said trigger signal. Consequently, the present embodiment is capable of precisely determining the amount of the labelling substance in the complex, thereby enabling highly accurate quantative determination of the object substance in the specimen, without influence of noise components such as bubbles and dusts in the conventional case.

The following experiment was conducted to verify the effect of the above-explained embodiment. An aqueous dispersion of magnetic polystyrene particles, containing magnetite therein and having a particle size of 1.0 μm and a particle concentration of 0.5 wt. %, was diluted 10,000 times and measured by said apparatus. For comparing the conventional method and the method of the present embodiment, the number of the trigger signals generated by the intensity of the forward scattered light was at first measured for 30 seconds, and the number of the trigger signals generated by the magnetic intensity obtained from the magnetic sensor 21 was then counted similarly for 30 seconds. As a result, the obtained count was higher, by about 20%, in the conventional method based on the trigger signals resulting from the forward scattered light. The higher count is considered to be ascribable to the noise components, such as dusts and bubbles contained in the aqueous dispersion and having given rise to additional counts. As explained above, the use of the magnetically labelled particles enabled high precise detection with a high S/N ratio.

Modifications

The present invention is not limited to said embodiments but is subject to various modifications. For example, a radioactive substance can be utilized for labelling the carrier particles, which can be identified by the detection of the radioactive intensity. In such case, the detector for radioactivity can be positioned in the same manner as the magnetic sensor 21 shown in FIG. 7.

Also, in said embodiments, the second substance is labelled with a fluorescent substance, but the effect of the present invention can be attained also by labelling the second substance with another substance such as a harmonic generating substance, a magnetic substance or a radioactive substance and employing a different labelling for the carrier particles.

What is claimed is:

1. A method for measuring a specimen in the presence of noise components comprising the steps of:

(a) preparing a first reagent formed by binding a first substance which binds to a specified component in the specimen, with carrier particles, and a second reagent formed by labelling a second substance which binds to said specified component with a first label said first label being a fluorescent substance, said carrier particles being labelled with a second label different from said first label;

(b) reacting the specimen with said first reagent having said second label and said second reagent having said first label to form complexes of a reaction product in a sample liquid which sample liquid optionally includes noise components;

(c) generating a laminar flow of said sample liquid to align components of said sample liquid present from said steps (a) and (b) along a sample liquid flow path;

(d) irradiating the aligned components of the sample liquid in the flow paths at an excitation wavelength to generate a forward scattered light signal from the complex and the noise components, a second signal from the second label of the carrier particles selected from the group consisting of a first fluorescent signal and a first harmonic wavelength forward scattered light signal and a second fluorescent signal from the first label which signal is distinguishable from said first fluorescent signal, wherein said second signal is a minimum threshold value for triggering detection of said second fluorescent signal; and (e) individually measuring the components of said sample liquid to measure said specified component, said measurement comprising the steps of detecting said second signal, and said second fluorescent signal in response to the second signal trigger; and measuring a fluorescent intensity of the detected second fluorescent signal from the first label to measure the presence of the specified component in the specimen.

2. A method according to claim 1, wherein the binding is based on an antigen-antibody reaction.

3. A method according to claim 1, wherein the binding is based on a nucleic acid hybridization reaction.

* * * * *

UNITED STATES PATENT AND TRADEMARK OFFICE
CERTIFICATE OF CORRECTION

PATENT NO.  : 5,601,983
DATED       : February 11, 1997
INVENTOR(S) : HIDEHITO TAKAYAMA ET AL.

It is certified that error appears in the above-identified patent and that said Letters Patent is hereby corrected as shown below:

COLUMN 1

Line 23, "virus" should read --viruses--.
Line 34, "wall.," should read --wall,--.

COLUMN 2

Line 12, "collect" should read --collecting--.

COLUMN 3

Line 56, "lecithine," should read --lecithin,--.

COLUMN 4

Line 28, "is" should be deleted.

COLUMN 7

Line 22, "Following" should read --The following--.

COLUMN 9

Line 27, "label said" should read --label, said--.

UNITED STATES PATENT AND TRADEMARK OFFICE
CERTIFICATE OF CORRECTION

PATENT NO. :   5,601,983

DATED      :   February 11, 1997

INVENTOR(S) :  HIDEHITO TAKAYAMA ET AL.     Page 2 of 2

It is certified that error appears in the above-identified patent and that said Letters Patent is hereby corrected as shown below:

<u>COLUMN 10</u>

Line 8, "paths" should read --path--.

Signed and Sealed this

Thirtieth Day of September, 1997

Attest:

BRUCE LEHMAN

Attesting Officer        Commissioner of Patents and Trademarks